United States Patent [19]

Macarthur et al.

[11] 4,009,280

[45] Feb. 22, 1977

[54] POWDER COMPOSITION FOR INHALATION THERAPY

[75] Inventors: Donald Ross Macarthur; David Ernest Smith, both of Loughborough, England

[73] Assignee: Fisons Limited, London, England

[22] Filed: June 9, 1975

[21] Appl. No.: 584,888

Related U.S. Application Data

[63] Continuation of Ser. No. 277,233, Aug. 2, 1972, abandoned.

[30] Foreign Application Priority Data

Aug. 10, 1971 United Kingdom ............ 37456/71

[52] U.S. Cl. ............................................... 424/283
[51] Int. Cl.² ............................................. A01N 9/28
[58] Field of Search .......................... 424/283, 216; 260/345.2

[56] References Cited

UNITED STATES PATENTS

| | | | |
|---|---|---|---|
| 3,121,096 | 2/1964 | Joly et al. | 260/345.2 |
| 3,484,445 | 12/1969 | Lee et al. | 260/345.2 |
| 3,629,290 | 12/1971 | Cairns et al. | 424/283 |
| 3,634,582 | 1/1972 | Hartley et al. | 424/14 |
| 3,671,625 | 6/1972 | Altounyan | 424/283 |
| 3,673,218 | 6/1972 | Cairns et al. | 424/283 |
| 3,686,412 | 8/1972 | Fitzmaurice et al. | 424/283 |
| 3,705,945 | 12/1972 | Fitzmaurice et al. | 424/283 |

*Primary Examiner*—Albert T. Meyers
*Assistant Examiner*—D. W. Robinson
*Attorney, Agent, or Firm*—Wenderoth, Lind & Ponack

[57] ABSTRACT

A powder composition comprising a mixture of the di-sodium salt of 1,3-bis(2-carboxychromon-5-yloxy) propan-2-ol having a mass median diameter in the range of 2 to 4, preferably 2.5 to 3.5 microns and a solid carrier acceptable in the lungs and having a particle size in the range of from 30 to 150 microns.

7 Claims, No Drawings

POWDER COMPOSITION FOR INHALATION THERAPY

This is a continuation application of application Ser. No. 277,233, filed Aug. 2, 1972, now abandoned.

This invention relates to a pharmaceutical powder composition for inhalation.

It is known that powder compositions may be administered by inhalation, using a device such as is described in British Pat. Specification No. 1,122,284. An example of such a form of device is one which comprises a hollow elongate housing having at both ends thereof one or more passageways adapted to permit the passage of air and having one end thereof adapted for insertion into the mouth and a propeller-like device rotatably mounted in the said housing on a rigid shaft mounted in said housing and co-axial with the longitudinal axis of the housing; said propeller-like device having, on the part thereof furthest from the end of the housing adapted for insertion into the mouth, mounting means adapted to receive a container, such as a gelatine or like capsule for the medicament to be inhaled.

While such devices are effective their effectiveness in providing the desired or optimum proportion of particles in the size range likely to penetrate into the lungs is sometimes proportional to the rate of flow of air through the device. Thus those patients who vary their pattern of inhalation (for example those who are infirm or too young to achieve a high rate of air flow) tend to receive a variable or low dosage of particles of the desired size. It is thus desirable that the proportion of particles emitted in the desired size range vary as little as possible with different rates of flow of air through the device. Furthermore, if the proportion of particles of the desired size emitted from the device can be increased the dosage of the drug in the capsule to be mounted in the device can be decreased with the consequent advantages.

According to the invention there is provided the di-sodium salt of 1,3-bis(2-carboxychromon-5-yloxy)propan-2-ol having a mass median diameter in the range of 2 to 4, preferably 2.5 to 3.5, microns.

According to the invention there is also provided a powder composition comprising a mixture of the di-sodium salt of 1,3-bis(2-carboxychromon-5-yloxy)propan-2-ol having a mass median diameter in the range of 2 to 4, preferably 2.5 to 3.5 microns and a solid carrier acceptable in the lungs and having a particle size in the range of from 30 to 150 microns. The composition is preferably substantially free of particles in the size range 11 to 29 microns. The particle sizes quoted herein for the di-sodium salt are those as measured with a suitable commercially available centrifugal sedimentometer, e.g. the "Simcar" Centrifugal Particle Size Analyser (Simcar Centrifuge), available from Simon-Carves Ltd., Stockport, England, and for the carrier are those as measured by sieving, e.g. with an "Alpine" Air-Jet Sieve.

In measuring particle sizes with a Simcar Centrifuge, the sample to be analysed is dispersed in a suitable liquid and centrifuged in a shallow disc centrifuge. Aliquots of the sedimenting suspension are withdrawn from a fixed point within the suspension at times in a fixed geometrical progression e.g. after centrifuging for 1, 2, 4, 8, 16 etc. minutes. The concentration of the sample for analysis in each of these aliquots is compared with the concentration in the suspension before centrifugation. The limiting particle size to which each aliquot is related can be determined using the Stokes' Equation modified for sedimentation under a centrifugal force, and further mathematical treatment (according to 'C. Slater and L. Cohen, A Centrifugal Particle Size Analyser, Journal of Scientific Instruments Vol. 39 pages 614–617, December 1962') is applied to these results to produce the particle size distribution curve and hence the mass median diameter of the sample for analysis.

The composition may also contain medicaments other than the di-sodium salt, for example a bronchodilator such as isoprenaline sulphate. The other medicament is preferably of fine particle size.

The solid diluent or carrier in the composition will generally be a non-toxic water soluble material chemically inert to the di-sodium salt and will of course be acceptable for inhalation. The carrier has particle size in the range 30 to 150 microns, preferably 30 to 80 microns, more preferably 30 to 70, and especially 30 to 60 microns. Examples of solid diluents or carriers which may be used in the composition of the invention include inorganic salts, e.g. sodium chloride or calcium carbonate; organic salts, e.g. sodium tartrate or calcium lactate; organic compounds, e.g. urea, propyliodone; monosaccharides, e.g. lactose or dextrose monohydrate; disaccharides, e.g. maltose or sucrose; polysaccharides, e.g. starches, dextrins or dextrans. A particularly preferred diluent or carrier is lactose, e.g. crystalline lactose.

As indicated earlier, it is especially desired that the composition be substantially free from particles having size in the range 11 to 29 microns. The term substantially free is used herein to denote that the composition contains less than 15%, preferably less than 10%, by weight thereof of particles having sizes in the range 11 to 29 microns.

The ratio of medicament to carrier may vary depending upon the materials used. The optimum ratio will depend upon the carrier and the method by which the composition is to be applied. We have found that the use of from 10 to 75% by weight of finely divided material to 90 to 25% by weight of carrier, preferably from 40 to 60% by weight of finely divided materials and from 60 to 40% by weight of carrier, e.g. about 50% by weight of medicament to 50% by weight of carrier, provides satisfactory results.

The finely divided di-sodium salt may be prepared by crystallisation, direct milling down to the desired particle size range and/or particle classification. The particulate carrier may be prepared by grinding the carrier and subsequently separating out the desired fraction by conventional methods, e.g. by air classification and sieving. The surface characteristics of individual particles of both the medicament and carrier may be modified by such conventional techniques as crystallisation, spray drying and precipitation.

The composition may be prepared from the fine and coarse ingredients by mixing the ingredients together in a mixer, e.g. a planetary mixer or a rotating blender. If desired, the surfaces of the particles of medicament and/or diluent and/or carrier may be coated with a pharmaceutically acceptable material, such as stearic acid, or polymers such as polyvinyl pyrrolidone. This coating procedure may serve incidentally to give a sustained release action to the medicament.

In addition to the medicament and carrier, the composition may contain other ingredients, such as colouring matter or flavouring agents such as saccharin, which are normally present in inhalant compositions. It is, however, preferred to use the minimum of such other ingredients.

The compositions according to the invention will generally be put up in gelatine, plastic or other capsules.

There is also provided, therefore, as a further feature of the invention, a dosage unit comprising a gelatine or like capsule containing a pharmaceutical composition according to the invention.

The amount of composition contained in the capsule will, of course, depend on the desired dosage. However, the capsule suitably contains from 10 to 300 mg. preferably from 10 to 100 mg of the composition, for example from about 10 to 30 mg. of the di-sodium salt in association with from about 10 to 30 mg. of carrier, e.g. coarse lactose.

The compositions of the invention are useful in the prophylactic treatment of allergic asthma in man.

The invention is illustrated, but in no way limited by the following Example.

EXAMPLE

Commercially available ground crystalline lactose having an effective particle size of from 1 to 100 microns (less than 30% by weight greater than 60 microns, not more than 30% by weight less than 30 microns) was passed through an air classifier, set to remove material having a particle size of less than 30 microns. The product from the air classifier contained less than 4% by weight of material of less than 32 microns size. This product was then sieved through a sieve having a mesh aperture of 63 microns to produce a lactose product which contained less than 10% by weight of particle with a size less than 32 microns and less than 20% by weight with a particle size in excess of 63 microns as determined on an "Alpine" air jet sieve.

The di-sodium salt was ground in a fluid energy mill until the product had a mass median diameter within the desired range as measured by the "Simcar" Centrifuge.

Compositions containing the desired proportions of the coarse and fine materials were mixed together in a planetary mixer and the mixture then passed through a 30 mesh sieve to remove or break up agglomerated particles.

The compositions were then put up in gelatine capsules containing 20 mg of the di-sodium salt and 20 mg of lactose. The filled capsules were then mounted in the capsule holder of the powder insufflator of British Patent Specification No. 1,122,284 and pierced. The apparent particle size distribution of the di-sodium salt in the cloud delivered by the insufflator was determined using a modified version of the multistage liquid impinger described in British Patent Specification No. 1,081,881. The modifications incorporated in the present design were the addition of an extra impingement stage, and of a glass tube with a right angled bend approximately mid-way along its length. The extra impingement stage was added prior to the three stages described in the above Patent Specification and consisted essentially of a jet of internal diameter 2.5 cm and a collection plate of diameter 5 cm designed to give an effective cut-off of approximately 12 microns at an air flow rate of 60 litres per minute. The glass tube, also of internal diameter 2.5 cm abutted the external end of the jet of the extra stage, and was coated internally with a film of polyethylene glycol 400 to provide a retentive surface for impinging particles. The insufflator was inserted into the upper, horizontal end of the glass tube and air drawn through at 60, 80, 100 or 120 litres per minute for 30 seconds. Five capsules were treated in this manner at each air flow rate. The weight of the di-sodium salt collected on each stage of the impinger, on the glass tube, and on a filter paper positioned after the final stage was determined spectrophotometrically after solution in an appropriate volume of distilled water. A graph was drawn of cumulative weight percentage oversize against aerodynamic diameter by plotting the weight percentage of the di-sodium salt on each stage and all preceding stages against the 50% cut-off diameter for that stage. The weight percentage of the di-sodium salt delivered having an aerodynamic diameter less than 6.7 microns was read off from this graph and the actual weight of di-sodium salt having an aerodynamic diameter less than 6.7 microns was calculated from this figure and the total weight recovered from the multistage liquid impinger.

The results of this procedure are shown in the following table:-

| Air Flow rate device (liters per minute) | Mass median diameter of di-sodium salt microns | 1.3 | 2.8 | 3.0 | 3.4 | 3.9 |
| --- | --- | --- | --- | --- | --- | --- |
| 60 | | 2.2 | 8.2 | 5.4 | 7.4 | 6.5 |
| 80 | | 4.1 | 5.4 | 6.2 | 6.0 | 6.9 |
| 100 | | 6.9 | 6.6 | 6.8 | 5.9 | 6.0 |
| 120 | | 6.9 | 6.5 | 6.3 | 6.2 | 4.2 |

Figures in the body of the Table show the weight (in mg) of the di-sodium salt delivered from the insufflator having an aerodynamic diameter less than 6.7 microns.

Particles having an aerodynamic diameter of less than 6.7 microns as measured by the multistage liquid impinger are those most likely to penetrate into the lungs of a patient.

We claim:

1. A powder composition for inhalation therapy which comprises from 10 to 75% by weight of the di-sodium salt of 1,3-bis(2-carboxy-chromon-5-yloxy)-propan-2-ol having a mass median diameter in the range of 2.8 to 3.9 microns, and from 90 to 25% by weight of a solid, pharmaceutically acceptable, water-soluble inhalation powder carrier which is chemically inert to the said di-sodium salt which carrier is acceptable in the lungs and has a particle size in the range of from 30 to 150 microns.

2. A composition according to claim 1 which contains less than 15 percent by weight of particles in the size range 11 to 29 microns.

3. A composition according to claim 1 containing a bronchodilator in addition to the di-sodium salt.

4. A composition according to claim 1 wherein the carrier has an effective particle size in the range 30 to 80 microns.

5. A composition according to claim 1 wherein the carrier is lactose.

6. A dosage unit comprising from 10 to 300 mg. of a composition according to claim 1.

7. A powder composition for inhalation therapy which comprises from 10 to 75% by weight of the di-sodium salt of 1,3-bis(2-carboxy-chromon-5-yloxy)-propan-2-ol having a mass median diameter in the range of 2.5 to 3.5 microns, and from 90 to 25% by weight of a solid, pharmaceutically acceptable, water-soluble inhalation powder carrier which is chemically inert to the said di-sodium salt which carrier is acceptable in the lungs and has a particle size in the range of from 30 to 150 microns.

* * * * *